United States Patent [19]

Balmat

[11] 4,431,486

[45] Feb. 14, 1984

[54] AZEOTROPIC DISTILLATION OF HYDROXYACETIC ACID

[75] Inventor: Jean L. Balmat, Kennett Square, Pa.

[73] Assignee: E. I. Du Pont de Nemours and Company, Wilmington, Del.

[21] Appl. No.: 367,753

[22] Filed: Apr. 12, 1982

[51] Int. Cl.³ .............................................. B01D 3/36
[52] U.S. Cl. ..................................... 203/69; 562/518; 562/580
[58] Field of Search ............... 562/518, 577, 579, 580; 203/28, 34, 35, 69, DIG. 6

[56] References Cited

U.S. PATENT DOCUMENTS

| | | | |
|---|---|---|---|
| 2,152,852 | 4/1939 | Loder | 260/535 |
| 2,153,064 | 4/1939 | Larson | 260/530 |
| 2,265,945 | 12/1941 | Loder | 260/530 |
| 2,334,524 | 11/1943 | Wenker | 562/580 |
| 2,443,482 | 6/1948 | Stattuck | 260/535 |

*Primary Examiner*—Frank Sever

[57] ABSTRACT

The yield of hydroxyacetic acid produced from formaldehyde, water and carbon monoxide in the presence of a sulfuric acid catalyst and using crude recycled hydroxyacetic acid as the reaction medium is improved by azeotropic distillation of crude, recycle hydroxyacetic acid with toluene. The distillation step reduces the water content of feed thereby increases conversion of formaldehyde to hydroxyacetic acid and reduces formic acid content in the product.

3 Claims, No Drawings

AZEOTROPIC DISTILLATION OF HYDROXYACETIC ACID

FIELD OF THE INVENTION

This invention relates to an improved process for the production of hydroxyacetic acid. More particularly, it relates to the azeotropic distillation with toluene of crude, recycle hydroxyacetic acid.

BACKGROUND OF THE INVENTION

Hydroxyacetic acid can be synthesized by the carbonylation of formaldehyde and water in an organic acid, usually hydroxyacetic, with sulfuric acid as a catalyst at pressures between 6,000 and 10,000 psig, and temperatures of 210° to 240° C., preferably 220° C. The carbonylation process is well known and is described in U.S. Pat. Nos. 2,153,064; 2,152,852 and 2,037,654. Conversion of the formaldehyde to hydroxyacetic acid is approximately 75%. The largest loss of formaldehyde is due to by-product formation; for example, formic acid.

This process produces a crude hydroxyacetic acid which must be purified prior to use or sale. Presently the crude acid can be purified in a four-step process as disclosed in U.S. Pat. No. 3,859,347. It is first treated with granulated, activated carbon for decolorization, then treated in a weak anion resin column to remove the sulfuric acid, subjected to live steam stripping to remove low-boiling impurities and finally treated with a cation exchange resin to remove metals present, e.g., iron or copper.

More specifically, crude hydroxyacetic acid is produced as expressed by the formula:

$$H.CHO + CO + H_2O \xrightarrow{H+} HO.CH_2COOH$$

A typical liquid mixed feed containing 10.9% formaldehyde, 23.9% water, 1.3% sulfuric acid and 63.9% organic acids, preferably hydroxyacetic acid, and using typical reaction conditions results in about a 75% conversion of formaldehyde to crude hydroxyacetic acid. The liquid mixed feed is a 1 to 3 ratio of 58% formaldehyde to recycled crude acid product. An excess of carbon monoxide is used to assist in the complete conversion of the formaldehyde. The water contributed to the mixed feed by the addition of the aqueous formaldehyde accounts for the presence of only approximately 8.0% of the water content. The difference between the 23.9% water content of the feed and the 8.0% is due to the water content of the recycle stream for the following reasons:

(a) In 58% aqueous formaldehyde the water to formaldehyde molar ratio is 1.2 to 1; therefore, there is an excess of 0.2 mole of water for each mole of formaldehyde based on the stoichiometry of the reaction.

(b) The product of synthesis is not free hydroxyacetic acid but a mixture of free hydroxyacetic acid and hydroxyacetic acid self-ester in a molar ratio of at least 0.7 to 0.3. This represents at least 0.3 mole of water unused in the reaction. The molar ratio of water to hydroxyacetic acid in the recycle stream because of (a) and (b) is about 0.5, making the water content 10.6% by weight. When this recycle stream is added to 58% aqueous formaldehyde in a weight ratio of 3 to 1, the resulting composite feed contains at least 18.5% water.

(c) Methyl formate and methoxyacetic acid, two by-products of hydroxyacetic acid synthesis, are formed by reactions having a water to formaldehyde molar ratio requirement of only 0.5 to 1, thereby increasing the water content of the recycle stream:

$$2H.CHO + 2H_2O \longrightarrow$$

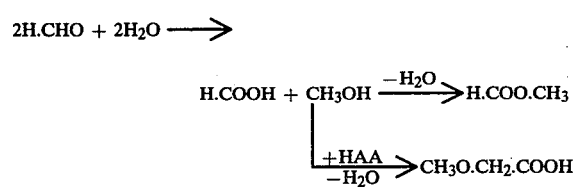

The sum of the effects described in (a), (b) and (C) accounts for the approximately 23.9% water in the feed a water to formaldehyde molar ratio in the mixed feed of 3.0 to 1 to 3.6 to 1.

The hydroxyacetic acid made by the above carbonylation and purification processes is typically a light yellow, 70% aqueous solution and of the following composition in weight percent.

| | |
|---|---|
| Total Acid as HAA (%) | 70.0–72.0 |
| Free Acid as HAA (%) | min. 62.4 |
| Formic Acid (%) | max. 0.45 |
| Ash (%) | max. 0.30 |
| Suspended Matter by Volume (%) | max. 0.015 |
| Color (Gardner) | max. 5 |
| Iron as Fe (mg/kg) | max. 10 |
| Copper as Cu (mg/kg) | max. 5 |
| Chloride as Cl (mg/kg) | max. 10 |

Hydroxyacetic acid is a useful commercial acid which is typically used to remove milkstone, to polish metals and remove corrosion from pipes.

SUMMARY OF THE INVENTION

It has been found that the yield of hdyroxyacetic acid produced from formaldehyde, water and carbon monoxide in the presence of a sulfuric acid catalyst and a relatively high reaction temperature and pressure using crude hydroxyacetic acid as the reaction medium is improved by reduction of the water to formaldehyde molar ratio to the range of 1.3:1 to 1.5:1.

Modification of the process to reduce the water to formaldehyde molar ratio can be accomplished in two ways: (a) remove water from the recycle stream and continue to use 58% aqueous formaldehyde, or (b) use a mixture of 58% aqueous formaldehyde and anhydrous formaldehyde in the feed. Use of (b) a mixture of aqueous and anhydrous formaldehyde containing 70 to 72% formaldehyde would provide an optimum water to formaldehyde molar ratio of 0.6 to 1 to 0.7 to 1. The anhydrous formaldehyde could be added as the low molecular weight polymer, paraformaldehyde or as the anhydrous monomer vapor by heating a formaldehydecyclohexanol adduct. Considering the cost however for 58% aqueous formaldehyde, paraformaldehyde and anhydrous formaldehyde from the cyclohexanol adduct combination, this approach would be uneconomical even if the conversion of formaldehyde to hydroxyacetic acid were increased to 85%. Removal of water from the recycle stream is the more practical solution to achieve an improved water to formaldehyde ratio.

It has now been found that an azeotropic distillation of the crude recycle hydroxyacetic acid results in the reduction in the water to formaldehyde ratio of the composite feed to a ratio in the range of 1.3 to 1 to 1.5 to 1, thereby increasing the conversion of formaldehyde to hydroxyacetic acid. The distillation process also results in the reduction of the by-product formic acid impurity in the product thereby replacing the steam stripping step for the removal of volatile impurities and importantly, greatly reducing the waste incineration costs.

To remove water from crude recycle hydroxyacetic acid by azeotropic distillation optimizes the water to formaldehyde ratio of the feed and simultaneously removes the impurity formic acid in the same manner.

DETAILED DESCRIPTION OF THE INVENTION

Any azeotropic agent for efficient removal of both water and formic acid is suitable for use in the process. Examples of such agents are aromatic hydrocarbons. The preferred agent is toluene.

Distillation within approximately a head temperature of 85° C. and a pot temperature of 130° C. will result in
(a) a composite feed with a water to formaldehyde molar ratio of about 1.3 to 1,
(b) a product after dilution to about 70% hydroxyacetic acid meeting the specification for formic acid concentration, and
(c) a light yellow product containing substantially no unhydrolyzable hydroxyacetic acid.

Crude hydroxyacetic acid is subjected to azeotropic distillation. About 25% of the distillate is withdrawn as semirefined product. The remaining 75% of the distillate is recycled to the reactors and serves as the reaction medium. The composite liquid feed consisting of recycled, crude hydroxyacetic acid, 58% aqueous formaldehyde and sulfuric acid would have a water to formaldehyde molar ratio of approximately 1.3 to 1 to 1.5 to 1 instead of the typical process ratio of 3.0 to 1 to 3.6 to 1.

A more detailed description of the invention is as follows:

The liquid feed to the hydroxyacetic acid process can be prepared in a mix tank from 58% formaldehyde and recycled product in a weight ratio of 1 to 3. Feed and carbon monoxide at a range of 6,000 to 10,000 psig, preferably, 7,500 psig are preheated to 190° to 210° C. before entering silver-lined tubular converters maintained at about 220° C. The pumping rate of the feed through the converters produces a reaction contact time of about 90 seconds.

The reaction product is cooled and sent to a separator where excess carbon monoxide is released from the liquid product. The gas phase is scrubbed with water and vented.

The resulting crude product is pumped to a distillation column for the removal of water and formic acid by azeotroping preferably with toluene. The overhead from the distillation column containing an azeotropic agent, formic acid, and water is cooled before being sent to a separator. A lower layer in the separator, containing water and formic acid, is disposed of by incineration. An upper layer of azeotropic agent is returned to the distillation column for reuse. Bottoms from the distillation column are product containing reduced concentrations of formic acid and water. Two-thirds of the product, after being cooled, is recycled to the mix tank and one-third undergoes further purification by passage through a carbon column, anion exchanger, and cation exchanger for the removal of tar, color, sulfuric acid, and metals as described in U.S. Pat. No. 3,859,349. The final product is a 70% aqueous solution of hydroxyacetic acid.

It is estimated that the removal of water and formic acid by azeotropic distillation would make a 10% absolute increase in the yield of hydroxyacetic acid from formaldehyde and significantly reduce the cost of purification.

The following examples are offered to illustrate the process of the invention.

EXAMPLE I

The following two experiments were performed to determine if azeotropic distillation of water from crude recycled hydroxyacetic acid could be achieved using an aromatic hydrocarbon agent such as toluene. The distillation was achieved with favorable results and the hydroxyacetic acid product can be recycled or fed to a conventional hydroxyacetic acid process. Simulated plant scale operations show that a water to formaldehyde desired molar ratio of 1.3 to 1 to 1.5 to 1 can be obtained.

A spinning band distillation column was fitted with a 3 neck-flask that accommodated a thermometer and an addition funnel.

156.3 g of 70% aqueous hydroxyacetic acid +15 ml of toluene was charged to the pot. Distillation at atmospheric pressure was performed. Toluene was added periodically to the pot at the same rate as it was being removed by distillation. The distillate collected had two phases: lower aqueous phase and the upper toluene phase.

The goal was to collect 47 mls of aqueous phase (30% of 156.3 g of aqueous hydroxyacetic acid) and not allow the pot temperature to exceed 125° C.

The following represents the volume relationship between the aqueous and toluene layers as it was collected in about 50 ml fractions.

| Distillate Fraction | Aqueous Layer (ml) | Toluene Layer (ml) |
|---|---|---|
| 1 | 8 | 42 |
| 2 | 8 | 42 |
| 3 | 9 | 41 |
| 4 | 6 | 44 |
| 5 | 7 | 43 |
| 6 | 8.5 | 41.5 |
|   | 46.5 | 253.5 |

On the basis of these results the azeotrope was 53.6 mole % $H_2O$ or 18.5 wt % $H_2O$. Analysis of the pot residue was

| 2.67 wt % $H_2O$ | 1.24% toluene |
|---|---|
| 101.0 wt % hydroxyacetic acid | |

The >100% for the hydroxyacetic acid was due to a portion of the hydroxyacetic acid being in the pot sample as the self-ester but reported after alkaline hydrolysis as the free acid.

Azeotropic distillation was effective in lowering the $H_2O$ content from 30% to 2.67%.

EXAMPLE II

The sample used in the following run contained in addition to water, the sulfuric acid catalyst and formic acid impurity to be expected in crude hydroxyacetic acid. The experimental conditions were the same as those for Example I.

Composition of starting material:

| | |
|---|---|
| 115.0 g | 70% aqueous hydroxyacetic acid |
| 1.87 g | $H_2SO_4$ |
| 3.75 g | H.COOH |

The distillation was terminated when 38.2 mls of lower phase were collected: this represents the sum of the $H_2O$ and H.COOH present in the starting material.

| Distillate Fraction | Aqueous Layer (ml) | Toluene Layer (ml) |
|---|---|---|
| 1 | 10 | 40 |
| 2 | 8.5 | 41.5 |
| 3 | 8.5 | 41.5 |
| 4 | 6 | 44 |
| 5 | 5 | 43 |
| 6 | 2.5 | 15 |
| | 40.5 | 225 |
| | (40.5 g) | (196.0 g) |

| Analysis of pot residue (74.5 g) | | |
|---|---|---|
| formic acid | 1.10% | 0.34% toluene |
| water | 3.77% | |
| hydroxyacetic acid | 95.8% | |

When formic acid is reduced to 0.45%, the toluene extraction serves the same function as steam stripper as well as removes the water from the recycle stream.

I claim:

1. In a process for the production of hydroxyacetic acid from formaldehyde, water and carbon monoxide in the presence of a sulfuric acid catalyst using crude, recycled hydroxyacetic acid as a reaction medium the improvement comprising an azeotropic distillation with essentially a single aromatic hydrocarbon of the crude hydroxyacetic acid to be recycled as reaction medium in amounts sufficient to cause an azeotrope with said hydroxyacetic acid.

2. A process of claim 1 wherein the aromatic hydrocarbon is toluene.

3. In a process for the production of hydroxyacetic acid from formaldehyde, water and carbon monoxide in the presence of a sulfuric acid catalyst using crude hydroxyacetic acid as a reaction medium the improvement comprising an azeotropic distillation with an aromatic hydrocarbon consisting essentially of toluene of the crude hydroxyacetic acid to be recycled as reaction medium in amounts sufficient to cause an azeotrope with said hydroxyacetic acid and a molar ratio of water to formaldehyde feed mix is 1.3 to 1 to 1.5 to 1.

* * * * *